Figure 1:
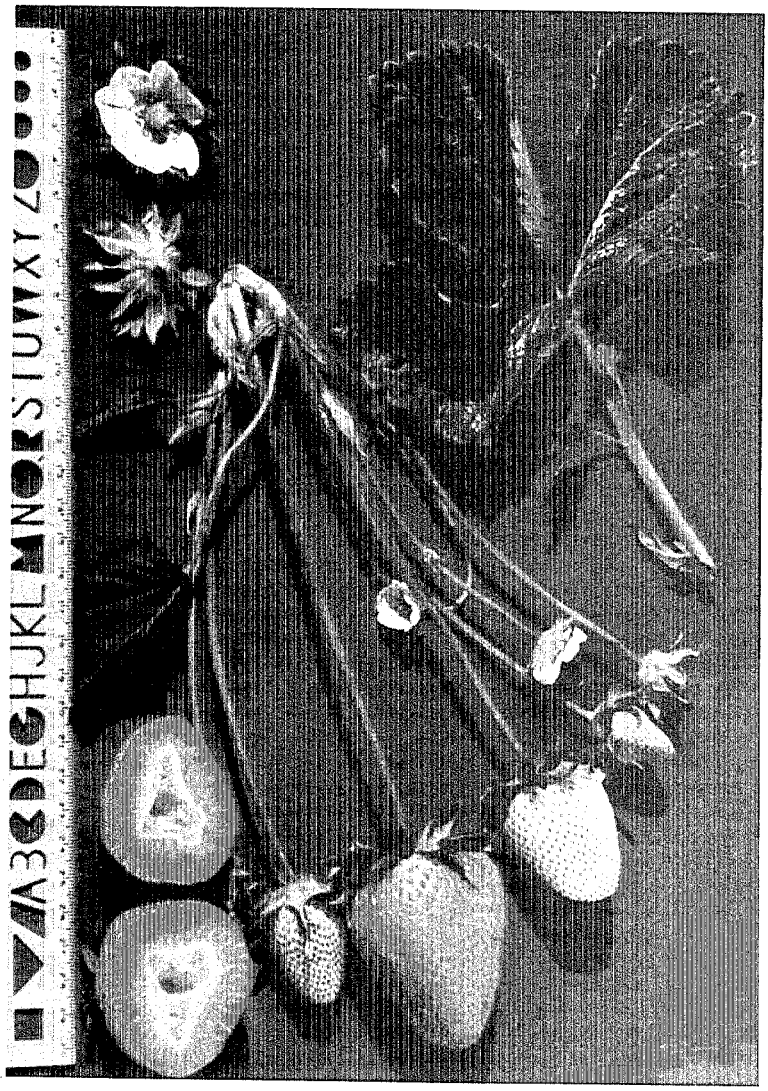

US00PP09130P

United States Patent [19]

Sjulin et al.

[11] Patent Number: Plant 9,130

[45] Date of Patent: May 9, 1995

[54] STRAWBERRY PLANT CALLED 'BALBOA'

[75] Inventors: Thomas M. Sjulin, Aromas; Amado Q. Amorao, Camarillo; Joseph I. Espejo, Jr., Watsonville, all of Calif.

[73] Assignee: Driscoll Strawberry Associates, Inc., Watsonville, Calif.

[21] Appl. No.: 285,388

[22] Filed: Aug. 3, 1994

[51] Int. Cl.[6] ..... A01H 5/00

[52] U.S. Cl. ..... Plt./48

[58] Field of Search ..... Plt. 48, 49

*Primary Examiner*—James R. Feyrer

*Attorney, Agent, or Firm*—Townsend and Townsend Khourie and Crew

[57] ABSTRACT

'Balboa' is a spring bearing variety which produces smooth glossy, attractive, full colored fruit, both on the surface and in the juicy flesh and has a very good flavor.

The crop is medium early in southern and central California and has the ability to produce a high volume of fruit in March, April and May in southern California, if the transplant is given proper chilling before being planted.

If grown in central California, the plants have the ability to continue production in the summer and fall. The plant is characterized by being medium dark and becoming large by summer. When vigorous, it is common to have one or more leaves per plant produce four leaflets per leaf instead of the normal three.

The fruit of the plant is also characterized by a large, dark calyx on primary berries which often produce a double row of serrated sepals. These sepals often become curled and are held irregularly, with narrow sepals, when present, held on the row away from the fruit, not next to the fruit.

1 Drawing Sheet

DESCRIPTION

This invention relates to a new and distinct short day winter-planted spring bearing variety of strawberry plant named 'Balboa' which is the result of a cross of the patented variety known as 'Swede', U.S. Plant Pat. No. 6,191 and the variety 'Douglas,' U.S. Plant Pat. No. 4,487. The variety is identified as *F.* X *ananassa* Duch.

The seedlings resulting from the aforementioned cross were multiplied by stolen runners in Shasta County, Calif. in a propagating nursery owned by Driscoll Strawberry Associates (DSA). Runner plants of each seedling clone were taken for testing to fruiting beds on other properties of DSA. The runners from clones of the seedling held in Shasta County propagating nursery were set for further testing on the property of DSA. These tests indicated the merits of the selection identified as 3V23 and it became a promising test variety. Subsequent tests of 3V23 on DSA controlled land proved that the selection had commercial value in California, and it was named 'Balboa'. Thereafter, 'Balboa' was asexually reproduced by stolon runners at DSA's propagating nursery in Shasta County, Calif.

IN THE DRAWING

FIG. 1 is a photograph taken on Apr. 15, 1994 in Oxnard, Calif., which illustrates plant parts of the new variety, typical in size, shape and color.

The inflorescence and the fruit shown in the drawing represent the main crop, not the crown crop. The crown crop comes from flowers that are initiated in the plant grown at the nursery before being transplanted and the main crop comes from flowers initiated when the plant is growing in the fruiting bed. The berry, in cross section, illustrates flesh color and a characteristic core cavity. The leaf shown is typical, with bracts present on the petiole. In the drawing there are three leaflets per leaf illustrated, but one or more leaves per plant will often have four leaflets per leaf. When plants are vigorous, often half or more of the plants will have leaves with four leaflets. The leaflet size is typical and the serrations pictured are moderately deep, but do not have an acute apex. These serrations are deeper, however, than the 'Joe Reiter' variety, U.S. Plant Pat. No. 5,300.

On May 19, in Oxnard, Calif., the average depth of the 'Balboa' leaf serrations was 5.05 mm and 'Joe Reiter' was 4.18 mm. At this date, the central leaflet of 'Balboa' was 7.6 cm wide and 7.6 cm long, while 'Joe Reiter' was 6.2 cm wide and 6.8 cm long. The petiolule of 'Balboa' was 9.4 mm and 'Joe Reiter' was 7.2 mm. The petiole of 'Balboa' was 12.7 cm and 'Joe Reiter' was 16.6 cm.

The primary berry illustrated in the drawing has a smooth surface with two shallow longitudinal furrows visible and no seedy tips at its apex. The primary berry is long conic in outline and the secondary berries are long wedge in outline as described in the U.S.D.A. Bulletin number 1043. These characteristics are typical of berries during this spring period. Primary berries of subsequent crops may be wedge shaped with areas of the apex coming to a plant but remain typically wedge shaped in outline. Also, during the spring period of 1994 in Oxnard, Calif., there is a very short to nonexistent common peduncle and the pedicel holding the primary and secondary berries appears to originate at the crown as illustrated in the drawing. The flesh of the new variety is darker in color, juicier, and usually equal in taste tests to the variety 'Joe Reiter'. Both varieties are considered to have excellent dessert qualities (See Table #1). The fruit size and crown crop of the new variety is equal to or greater than that of 'Joe Reiter'. 'Balboa' had superior production and larger fruit size than 'Joe Reiter' (See Table #3).

While 'Joe Reiter' and 'Balboa' are considered moderately low chilling varieties, they are not as low chilling as 'Chandler', U.S. Plant Pat. No. 5,262, and are not considered as early in production as 'Chandler'. Both 'Joe Reiter' and 'Balboa' produce their first ripe crown crop berries two weeks after 'Chandler'. The fruit of 'Chandler' during this early period is rougher than 'Balboa' or 'Joe Reiter'. 'Balboa' is less rough than the 'Joe Reiter' during this period.

By the middle of May in Oxnard, Calif., often the time when strawberry fruit production is converted to processing from the fresh market, the production of 'Balboa' is greater than 'Joe Reiter'. Tests in Oxnard produced 723 gms per plant for 'Balboa' compared to 641 gms per plant with 'Joe Reiter' by mid May if both varieties are given their correct chilling at the nursery and cold storage before being planted. During the crown crop, the 'Balboa' plant is smaller than 'Joe Reiter' and may become equal in site during the main crop.

The major differences between 'Balboa' and 'Douglas', one of the parents of 'Balboa', are plant type and production during late summer and fall and fruit shape and firmness. 'Balboa' produces more fruit during late summer and fall and becomes less vegetative during this period. The shape of 'Balboa' is more conic and less wedged shaped than 'Douglas' and its skin and flesh are firmer than 'Douglas'.

The 'Balboa' variety is very dependent on having adequate chilling before being planted and especially in southern Calif. If insufficient chilling is given, this variety becomes very susceptible to *Xanthomas fragariae* and the plant becomes weak, giving poor total production.

The fruit of 'Balboa' is darker inside and out and its size during the total fresh market season is larger than the 'Joe Reiter'. The fruit production during the processing period, mid May through the first week in July, is usually equal to that of 'Joe Reiter' and reaches 450 gms per plant.

In central California after May, the plant of 'Balboa' becomes larger than DSA's variety 'Commander', U.S. Plant Pat. No. 7,024. The leaves of 'Balboa' are glossy but not as glossy as 'Commander'. The leaflet serrations are mostly deeper and the petiolules are longer than 'Commander' but there are not consistent differences in the central leaflet size. The hair on pedicels next to the fruit is perpendicular to the pedicel of 'Swede', DSA's variety, U.S. Pat. No. 6191 which is one parent of 'Balboa', and on 'Balboa' the hair is parallel. 'Swede's' inflorescence is shorter than 'Balboa'. 'Balboa's' fruit has darker flesh than 'Swede' or 'Commander' and the skin is darker than 'Commander', but equal to 'Swede' and more uniform in color. 'Swede' fruit has more splits at its apex than 'Balboa'. The fruit size of the crown crop of 'Balboa' is not as large as 'Swede' or 'Commander', but there are less mis-shaped primaries on 'Balboa'. The skin of 'Balboa' after May is not as firm as 'Commander'. Sepals of primary berries of 'Balboa' are darker, more serrated, and more prone to be irregularly curled than 'Swede' or 'Commander'.

The crown crop of 'Balboa' usually comes the first week in April, about the same time as 'Commander', but not as early as 'Swede'. Flavor panels have rated both 'Balboa' and 'Commander' very good. (See Table #2).

Table #4 summarizes the major differences between 'Balboa' and 'Joe Reiter' in southern California. Table #5 summarizes differences between 'Balboa' and the 'Commander' and 'Swede' in central California.

Flavor panel summary readings of 'Balboa' compared to the 'Commander' variety are listed on Table #2 and demonstrate the high dessert quality of the 'Balboa' variety.

The 'Balboa' plant is susceptible to *Xanthomonas fragariae,* verticillium wilt and the anthracnose disease caused by *Collectotrichum acutatum* and is moderately tolerant of powdery mildew. As a seeding and selection it withstood noticeable injury from the natural infection of the known common virus components of California. The plant is susceptible to injury from the two spotted spider mite as well as flower thrip. The fruit of 'Balboa' is susceptible to the decay organisms, Botrytis and Rhizopus.

The varietal characteristics of the novel plant described in detail were observed at various times of the year, but specific measurements are qualified by the time of year and location. Flavor and soluble solid ratings also vary during the season and in some cases vary from location to location. All measurements and descriptions were taken from the first year plants dug at a high elevation nursery during October and planted at fruiting beds during late October or early November. Many characteristics such as plant size, crop, fruit size, shape and color will vary during the spring, summer and fall.

The color terminology is in accordance with the Munsell color system.

SPECIFIC DESCRIPTION

Morphological measurements, soluble solid readings as well as flavor test ratings, as seen below, vary depending on time of the year and location. Even though measurements and ratings are qualified by time and location, if a final statement is made, that statement is also qualified. Statements regarding varietal differences in these characters become valid when there are consistent differences regardless of the actual measurement or rate at a given time of year.

Plant: Medium to large in size if given ample chilling before being planted. Not considered a low chilling type, but will produce an adequate plant in southern California. In central California it also becomes medium to large in size and can reach 30 cm in height and 40 cm in width by the last of April when planted at the correct time, and still remain in a fruiting cycle the remainder of the first fruiting year.

Leaves: Medium to large in size. In Watsonville, the central leaflet averages 7.12 to 6.87 in width and length in early April with serrations that are moderately deep averaging 5.05 mm, with an apex that is moderately acute at the apex.

After April in Oxnard, the central leaflet averages 7.6 cm in length and width. The serration depth averages over 6 mm during the late summer in Santa Maria. Petioles are considered short in Oxnard during March and April crop but becomes 12 to 13 cm in length during May and become over 19 cm in the fall in Santa Maria when measurements are made from and including stipules to the petiolule. Petiolules moderate in length averaging over 9 mm in May in Oxnard. Bracts on petioles may or may not be present. After the crown crop of a winter planting, four leaflets may form on one or more leaves on each plant instead of three. The presence of four leaflets has become a noticeable identification of 'Balboa'. Color of upper side of leaflet is 9.3 GY–3.0/6.8. Lower side is 9.5 GY –7.9/11.0.

Isozymes in Leaf Extract: Phosphoglucoisomerase (PG1) AI Leucine aminopeptidase (LAP) B3. Phosphoglucomutase (PGM) C2. This testing was done by the Driscoll Strawberry Associates laboratory following procedure described in the publication: Electrophoretic Characterization of California Cultivars, by Bringhurst — 1981 (See Table 4 and 5).

Runners: Runners are vigorous and considered abundant at the nursery and also in fruiting beds if given more than ideal chilling before or after being transplanted.

Inflorescence: Medium in length, short during the crown crop and becoming longer during late summer, ranging from 29 to 38 cm with an average of 33 cm in total length in Santa Maria. The common peduncle during the Spring, even to the end of May, is short, often 5 cm or less in length with pedicels holding primary and secondary berry quite long, 5 to over 20 cm in length. In late May in Watsonville, primary flowers including the calyx, become 50 mm or more in diameter with an average of 6.6 petals per flower. During this period the petal width of primary flowers average 17.5 mm and the pistils average 9.9 mm in diameter. Hair on pedicels irregularly parallel to the pedicel at the point where the pedicel joins the fruit, but the hair on the common peduncle of the same inflorescence at the union with the crown, is perpendicular to the peduncle. During summer and fall, the pedicel holding the primary berry may originate from the axil of two peduncles or may originate from one of the peduncles.

Fruit: Crown crop size is large in southern California and medium in size in central California. Crown crop primaries in southern California average 47 mm in length and 38 mm in width. The average weigth per berry in Oxnard by April 9 is 30.9 gm on plantings that have ideal plant growth and production for the area. In central California this weight by May 18, is 31.8 gms. By June 10 in Oxnard, the average weight per berry is 24 gms. The shape of crown crop fruit has rounded shoulders as well as becoming round at the apex and is smooth. The main crop primaries are more conic in outline with only slight longitudinal furrows present, but may be medium to long wedge with an area of the apex often coming to a point. Secondary and tertiaries berries have rounded shoulders, but may either be conic or medium to long wedge in outline. The skin and flesh is firm, but after May, holding test ratings become poorer, especially when too much nitrogen fertilizer has been applied. The color outside surface is 6.8 R-2.6/9.4 and inside it is 8.3 R-3.5/13.0 to 6.6 R-2.9/9.7 in width except around the core which is 7.7 R-5.5/16.4.

The aroma of fruit is equal to 'Commander' but not as strong as 'Swede'.

Seed: Medium in size and yellow except where exposed to full sun. The seed is held equal to or below the fruit surface and this slightly sunken seed character varies during the year.

Calyx: Large dark calyx on primary fruit and average 45 to 50 mm in diameter the crown crop in Oxnard, and become larger during the main crop, but average 34 mm during the fall crop in Santa Maria. Individual sepals of these primaries can vary in width from 4 mm to 13 mm on the same calyx. Individual sepals are often held uniformly on the calyx but can become curled and are held erratically. Some sepals are serrated at the apex and some overlapping occurs. Sepal color on the side facing fruit is 8.9 GY-2.3/4.7 to 7.4 GY-2.3/4.0. Overlapping of sepals occurs mainly on the primary flowers and when it occurs the narrow sepals are on the outside row, not on the inside next to the fruit.

TABLE #1

| OXNARD FLAVOR TEST SUMMARY, 1993 | | |
|---|---|---|
| | 'BALBOA' | 'JOE REITER' |
| FLAVOR* | 3.0 | 3.2 |

*Average of 10 flavor tests comparing 'Balboa' and 'Joe Reiter', done with fruit picked in Oxnard, CA and held in cold storage an average of 5 days before being rated. Ratings based on scores of 1 to 5, 5 being the best.

TABLE #2

| SANTA MARIA AND WATSONVILLE FLAVOR TEST SUMMARY (1993-1994) | | |
|---|---|---|
| | 'BALBOA' | 'COMMANDER' |
| FLAVOR* | 3.4 | 3.1 |

*Average of 4 flavor tests comparing 'Balboa' and 'Commander', done with fruit picked in Santa Maria and Watsonville, CA and held in cold storage an average of 5 days before being rated. Ratings based on scores of 1 to 5, 5 being the best.

TABLE #3

| OXNARD PRODUCTION THROUGH 4/2/94 | | |
|---|---|---|
| | 'BALBOA' | 'JOE REITER' |
| Number of Picks | 10 | 9 |
| Grams/Plant | 174.9 | 118.9 |
| Avg. Grams/Berry | 30.0 | 22.8 |
| % Culls | 16.8% | 15.5% |

TABLE #4

| Major Differences - Oxnard, California | |
|---|---|
| 'Balboa' | 'Joe Reiter' |
| PLANT: | PLANT: |
| 1. Darker than 'Joe Reiter'. | 1. Lighter than 'Balboa'. |
| 2. 4 leaflets per leaf is common. | 2. 4 leaflets per leaf not common. |
| 3. Bracts on petiole more common than 'Joe Reiter'. | 3. Bracts on petiole not as common as 'Balboa'. |
| 4. Isozyme Pattern PGI-AI LAP-B3 PGM-C2 | 4. Isozyme Pattern PGI-A4 LAP-B3 PGM-C4 |
| 5. Plant smaller than 'Joe Reiter' up to June. | 5. Plant larger than 'Balboa' up to June. |
| 6. Very susceptible to *Xanthomonas fragariae* when not given adequate chilling before planting. | 6. Not as susceptible to *Xanthomonas fragariae* as 'Balboa'. |
| INFLORESCENCE: | INFLORESCENCE: |
| 1. Calyx of primary flowers, when double row of sepals present: narrow sepals curled and are not next to fruit. | 1. Calyx of primary flowers, when double row of sepals present: narrow sepals not curled and are next to fruit. |
| 2. Sepals are darker in color than 'Joe Reiter'. | 2. Sepals are lighter in color than 'Balboa'. |
| 3. Serrated Sepals are common. | 3. Serrated Sepals not as common as 'Balboa'. |
| FRUIT: | FRUIT: |
| 1. Higher gloss than 'Joe Reiter'. | 1. Less gloss than 'Balboa'. |
| 2. Less seedy tips than 'Joe Reiter'. | 2. More seedy tips than 'Balboa'. |
| 3. Darker skin and flesh than 'Joe Reiter' - very good flavor. | 3. Lighter skin and flesh than 'Balboa' - very good flavor. |
| 4. Juicier flesh than 'Joe Reiter'. | 4. Drier flesh than 'Balboa'. |
| 5. Less short wedge in May than 'Joe Reiter'. | 5. Becomes short wedge in May. |
| 6. More fresh market production by early May than 'Joe Reiter' (same | 6. Less fresh market production by Early May than 'Balboa' (same environment). |
| | 7. Less susceptible to Botrytis than 'Balboa'. |

TABLE #4-continued

| Major Differences - Oxnard, California | |
|---|---|
| 'Balboa' | 'Joe Reiter' |
| environment). 7. More susceptible to Botrytis than 'Joe Reiter'. | |

TABLE #5

| Major Differences - Santa Maria and Watsonville, California | | |
|---|---|---|
| 'Commander' | 'Balboa' | 'Swede' |
| PLANT: | PLANT: | PLANT: |
| 1. Gloss to leaves: very glossy - darker than 'Balboa'. 2. Petiolule - length (May 1) 6 mm. 3. Leaflets per leaf: 4 leaflets per leaf not common. 4. Isozyme Pattern: PGI-A4 LAP-B3-PGM-C4 5. Plant equal to or smaller than 'Balboa' after May in same environment. | 1. Gloss to leaves: glossy - dark. 2. Petiolule - length (May 1) 10.3 mm. 3. Leaflets per leaf: 4 leaflets per leaf common. 4. Isozyme Pattern: PGI-A1 LAP-B3-PGM-C2 5. Plant becomes larger than 'Commander' or 'Swede' after May in same environment. | 1. Gloss to leaves: glossy - medium dark. 2. Petiolule length (May 1) 8.5 mm. 3. Leaflets per leaf: 4 leaflets per leaf not common. 4. Isozyme Patten: PGI-A1 LAP-B3-PGM-C2 5. Plant not as large as 'Balboa' after May in same environment. |
| INFLORES-CENCE: | INFLORES-CENCE: | INFLORES-CENCE: |
| 1. Calyx of primary flower: when double row of Sepals present narrow Sepals not curled and are next to fruit. | 1. Calyx of primary flower: when double row of sepals present narrow sepals curled and are not next to fruit. | 1. Calyx of primary flower: When double row of sepals present narrow sepals are not curled and are next to fruit. |

TABLE #5-continued

| Major Differences - Santa Maria and Watsonville, California | | |
|---|---|---|
| 'Commander' | 'Balboa' | 'Swede' |
| 2. Sepals are dark but not as dark as 'Balboa'. 3. Serrations on Sepals not as common as 'Balboa'. 4. Hair on pedicels next to fruit parallel to pedicel. 5. Much of fruit ripens farther from crown than outside leaves. | 2. Sepals are darker than 'Commander' or 'Swede'. 3. Serrated Sepals are common. 4. Hair on pedicel next to fruit parallel to pedicel. 5. Much of fruit ripens farther from crown than outside leaves. | 2. Sepals are lighter in color than 'Balboa'. 3. Serrations on Sepals not as common as 'Balboa'. 4. Hair on pedicel next to fruit perpendicular to pedicel. 5. Fruit ripens closer to crown than 'Balboa'. |
| FRUIT: | FRUIT: | FRUIT: |
| 1. Skin and flesh lighter than 'Balboa'. 2. Some fruit may become bullet shaped. 3. Primaries not prone to split at apex. 4. Seed usually equal to or exerted. 5. Primary berries large. | 1. Skin and flesh darker than 'Commander' and 'Swede.' 2. Calyx of secondaries may be slightly reflexed but fruit not bullet shaped. 3. Primaries not prone to split at apex. 4. Seed mostly equal to surface but may become inserted or exerted. 5. Primary berries large but not as large as 'Commander' or 'Swede'. | 1. Flesh lighter than 'Balboa' - skin may equal 'Balboa' color. 2. Calyx of secondaries not necked or bullet shaped. 3. Primaries prone to split at apex. 4. Seed mostly equal to surface or exerted. 5. Primary berries large. |

We claim:

1. The new and distinct variety of strawberry plant herein described and illustrated, and identified by the characteristics enumerated above.

* * * * *